(12) United States Patent
Gupte et al.

(10) Patent No.: US 10,081,597 B2
(45) Date of Patent: Sep. 25, 2018

(54) PROCESS FOR PREPARATION OF DEXMETHYLPHENIDATE HYDROCHLORIDE

(71) Applicant: Embio Limited, Mumbai (IN)

(72) Inventors: Ashutosh Digambar Gupte, Mumbai (IN); Sunil Vaman Joshi, Mumbai (IN); Amit Hari Pakhurde, Mumbai (IN)

(73) Assignee: Embio Limited, Mumbai (IN)

( * ) Notice: Subject to any disclaimer, the term of this patent is extended or adjusted under 35 U.S.C. 154(b) by 0 days.

(21) Appl. No.: 15/320,511

(22) PCT Filed: Nov. 3, 2014

(86) PCT No.: PCT/IB2014/065763
§ 371 (c)(1),
(2) Date: Dec. 20, 2016

(87) PCT Pub. No.: WO2015/198108
PCT Pub. Date: Dec. 30, 2015

(65) Prior Publication Data
US 2017/0217886 A1   Aug. 3, 2017

(30) Foreign Application Priority Data

Jun. 27, 2014 (IN) .................. 2090/MUM/2014

(51) Int. Cl.
*C07D 211/34* (2006.01)
(52) U.S. Cl.
CPC ........ *C07D 211/34* (2013.01); *C07B 2200/07* (2013.01)
(58) Field of Classification Search
CPC ................. C07D 211/34; C07B 2200/07
USPC ........................................ 546/238
See application file for complete search history.

(56) References Cited

U.S. PATENT DOCUMENTS

| | | | |
|---|---|---|---|
| 6,100,401 A * | 8/2000 | Prashad | C07D 211/34 546/233 |
| 6,162,919 A | 12/2000 | Prashad | |
| 9,063,100 B2 | 6/2015 | Nacson | |
| 9,204,460 B2 | 12/2015 | Orjmark et al. | |
| 2005/0277791 A1 | 12/2005 | Nishiyama et al. | |

FOREIGN PATENT DOCUMENTS

WO    1998025902    6/1998

OTHER PUBLICATIONS

Aldrich Catalogue ,1998-1999, p. 510, p. 699, 3 pages.*

* cited by examiner

*Primary Examiner* — Taylor V Oh
(74) *Attorney, Agent, or Firm* — Blueshift IP, LLC; Robert Plotkin

(57) ABSTRACT

The present invention relates to a process for preparation of dexmethylphenidate hydrochloride from racemic methylphenidate. The process involves the treatment of racemic mixture of dl-threo-methylphenidate base in the presence of di-pivaloyl-D-tartaric acid (D-DPTA) in a solvent to isolate dipivaloyl tartrate salt of d-threo-methylphenidate. The dipivaloyl tartrate salt of d-threo-methylphenidate is treated with a base to obtain a d-threo-methylphenidate base, which is extracted using a suitable solvent. The d-threo-methylphenidate base is treated with hydrochloric acid-isopropyl alcohol solution to obtain slurry of d-threo-methylphenidate hydrochloride also known as dexmethylphenidate hydrochloride. The dexmethylphenidate hydrochloride slurry is filtered and washed with acetone. The invention also discloses a process for recovery of D-DPTA from the salt mother liquor and from the spent aqueous layer. The process is economical, environmental friendly and results in increased yield and optically pure dexmethylphenidate hydrochloride.

10 Claims, No Drawings

PROCESS FOR PREPARATION OF DEXMETHYLPHENIDATE HYDROCHLORIDE

TECHNICAL FIELD OF THE INVENTION

The present invention relates to a process for preparation of dexmethylphenidate hydrochloride from racemic methylphenidate. The process involves the preparation of tartaric salts of methylphenidate and conversion of tartaric salts of methylphenidate to enantiomers of methylphenidate hydrochloride.

BACKGROUND OF THE INVENTION

Methylphenidate hydrochloride is a psychostimulant of phenethylamine class. The drug is safe, effective and approved for the treatment of attention-deficit hyperactivity disorder (ADHD), postural orthostatic tachycardia syndrome and narcolepsy in human. Long-term treatment with methylphenidate hydrochloride increases the activity of central nervous system, reduces the structural and functional abnormalities in the brain.

Dexmethylphenidate, also known as d-threo-methylphenidate (D-TMP) is a dextrorotatory enantiomer of methylphenidate, which is also effective psychostimulant against ADHD. Dexmethylphenidate is the (R,R) enantiomer of methylphenidate.

Racemic methylphenidate contains both dextro- and levorotatory methylphenidate, which are useful for the treatment of ADHD. It is very challenging to isolate a purified form of dexmethylphenidate.

Methylphenidate molecule contains two asymmetric centers and hence exists as four stereoisomers, two erythroisomers namely (R, S) and (S, R) and two threoisomers namely (R, R) and (S, S). Out of the four possible stereoisomers of methylphenidate, only threodiastereoisomers are used in modern practice. The eudysmic ratio between the threo (R, R) and (S, S) enantiomers of methylphenidate is high.

Different methods have been proposed in the state of art for the preparation of dexmethylphenidate hydrochloride using various chemical reactions and enzymatic resolution.

The United States patent numbered U.S. Ser. No. 09/204, 460 titled "Process for preparing the d-threo isomer of methylphenidate hydrochloride" discloses a process for preparing the d-threo isomer of methylphenidate hydrochloride. The process involves the conversion of d,l-threo methylphenidate hydrochloride to a free base form, resolving the free base with (R)-(−)-1,1'-binaphthyl-2,2'-diyl hydrogen phosphate to obtain the phosphate salt enriched with the d-threo isomer of methylphenidate, basifying the phosphate salt to obtain the free base form of d-threo methylphenidate, converting the free base into the hydrochloride salt form of d-threo methylphenidate in high optical purity. Finally, the salt prepared is recrystallized to obtain the desired d-threo isomer with optical purity. However, the process may not result in high yield of the product and the invention is silent with respect to the recovery of the resolving agent.

The PCT application numbered PCT/GB1997/003418 titled "The preparation of enantiomerically-enriched threo-methylphenidate" discloses a process for increasing the enantiomeric excess of an enantiomerically-enriched mixture of enantiomers of an acid addition salt of threo-methylphenidate. The process involves crystallization followed by partial dissolution of methylphenidate. The process involves the bioresolution of racemic methylphenidate in presence of the enzyme that exhibits enantioselectivity. The enzyme used in the present invention is alpha-chymotrypsin. The enzymatic separation may involve specific reaction conditions to achieve good yield of the product and hence process may involve additional precautions to obtain optically pure compounds with high yield.

The United States patent numbered U.S. Ser. No. 09/063, 100 titled "Process for preparing the d-threo isomer of methylphenidate hydrochloride" describes a process for preparing the d-threo isomer of methylphenidate hydrochloride comprising resolving the racemic mixture of threo methylphenidate hydrochloride with dibenzoyl-D-tartaric acid to obtain a dibenzoyl-D-tartrate salt enriched with the d-threo isomer of methylphenidate. The process involves the steps of resolving d,l-threo methylphenidate hydrochloride with 4-methylmorpholine and dibenzoyl-D-tartaric acid in the presence of dibenzoyl-D-tartrate salt enriched with the d-threo isomer of methylphenidate to obtain a dibenzoyl-D-tartrate salt enriched with the d-threo isomer of methylphenidate. The salt is basified to form a free base of d-threo methylphenidate. The free base is converted into hydrochloride salt of d-threo methylphenidate with high optical purity. Finally, the d-threo methylphenidate hydrochloride is recrystallized to obtain the desired d-threo isomer. However, the process may not result in increased yield of the product.

The existing processes for preparation of dexmethylphenidate hydrochloride are associated with disadvantages of repeatability of the process as well as the enantiomeric purity of the isolated dexmethylphenidate hydrochloride. In addition, many of the processes lack good yield of the product. Hence, there is a need for a process to prepare dexmethylphenidate hydrochloride with high yield and high enantiomeric purity.

SUMMARY OF THE INVENTION

The present invention discloses a process for preparation of dexmethylphenidate hydrochloride from the racemic mixture of threo-methylphenidate. The process involves the treatment of dl-threo-methylphenidate base with di-pivaloyl-tartaric acid (DPTA) as resolving agent using an organic solvent to obtain d-threo-methylphenidate DPTA salt. The d-threo-methylphenidate DPTA salt is further treated with aqueous ammonia solution to regenerate the d-threo-methylphenidate base, which is converted to hydrochloride by treatment with hydrochloric acid. The process results in production of highly pure enantiomer of dexmethylphenidate hydrochloride with high yield. The process is also more economical and environmental-friendly.

The present invention also discloses a process for recovery of L- or D-DPTA. The mother liquors of the salt formation reaction and the spent aqueous layers after extraction of d or l-threo-methylphenidate base from basification of the salts are used for recovery of L- or D-DPTA.

DETAILED DESCRIPTION OF THE INVENTION

Reference will now be made in detail to the description of the present subject matter with one or more examples. Each example is provided to explain the subject matter and not a limitation. Various changes and modifications obvious to one skilled in the art to which the invention pertains are deemed to be within the spirit, scope and contemplation of the invention.

In order to make the matter of the invention clear and concise, the following definitions are provided for specific terms used in the following description.

The term "Stereoisomer" means isomeric molecules that have the same molecular formula and sequence of bonded atoms (constitution) but differ only in the three-dimensional orientations of their atoms in space.

The term "Enantiomer" means one of two stereoisomers that are mirror images of each other that are non-superposable (not identical).

The term "Racemic mixture" means one that has equal amounts of left- and right-handed enantiomers of a chiral molecule.

The term "Resolving agent" means a chemical compound used to separate the racemic compounds into their enantiomers from the racemic mixture.

The term "Isomer" means each of two or more compounds with the same formula but a different arrangement of atoms in the molecule and different properties.

In the present invention, the enantiomer of dexmethylphenidate hydrochloride is prepared from the racemic mixture of threo-methylphenidate. Methylphenidate molecule contains two asymmetric centers, hence, exists as four stereoisomers, which includes two erythro isomers namely (R,S) and (S,R) and two threo isomers namely (R,R) and (S,S).

According to an embodiment of the invention, the racemic mixture dl-threo-methylphenidate base is treated with a resolving agent di-pivaloyl-D-tartaric acid (D-DPTA) in a suitable solvent. The solvent is selected from a group comprising acetonitrile, ethyl acetate, isopropyl acetate, acetone, methyl ethyl ketone, isobutyl methyl ketone, methylene chloride, ethylene dichloride, C1-C4 lower aliphatic alcohol or water. These solvents are either used alone or as a mixture of one or more solvents. The molar ratio of the D-DPTA to dl-threo-methylphenidate is in the range of 0.25:1 and 2:1, preferably between 0.85:1 and 1.25:1. The reaction is carried out at the temperature in the range of 30° C. to boiling point of the solvent used. The reaction results in D-DPTA salts of d-threo-methylphenidate and l-threo-methylphenidate. The less soluble salt of d-threo-methylphenidate precipitates out and it is isolated by filtration.

In another embodiment of the invention, di-pivaloyl-L-tartaric acid (L-DPTA) can also be employed with advantage as in previous embodiment of the invention. Here, the less soluble salt obtained is l-threo-methylphenidate. Pure d-threo-methylphenidate is isolated from the mother liquors and converted to hydrochloride by treatment with hydrochloric acid. The hydrochloric acid is used in the form of hydrochloric acid solution or hydrochloric acid gas.

In another embodiment of this invention, the D- or L-DPTA salt of d or l-threo-methylphenidate is dissolved in water and treated with a base at ambient temperature to regenerate the d or l-threo-methylphenidate base, which is extracted with a solvent and treated with hydrochloric acid to convert the base to d or l-threo-methylphenidate hydrochloride. The base used for the basification is selected from a group comprising sodium hydroxide, potassium hydroxide, sodium bi-carbonate, sodium carbonate, potassium carbonate, ammonium hydroxide and triethylamine. The solvent used for extraction of methylphenidate base is selected from a group comprising diethyl ether, diisopropyl ether, chloroform, methylene chloride, hexanes, ethylene dichloride, toluene, benzene, xylene, ethyl acetate and isopropyl acetate.

The invention also discloses a process for recovery of D- or L-DPTA. D- or L-DPTA are extracted from the mother liquors of the salt formation reaction and the spent aqueous layers after extraction of d or l-threo-methylphenidate base from basification of the salts. The mother liquors of the salt formation reaction are basified in aqueous solution with a base. The base is selected from a group comprising sodium hydroxide, potassium hydroxide, sodium bi-carbonate, sodium carbonate, potassium carbonate, ammonium hydroxide and triethylamine. The reaction mass is extracted with a solvent selected from a group comprising diethyl ether, diisopropyl ether, chloroform, methylene chloride, hexanes, ethylene dichloride, toluene, benzene, xylene, ethyl acetate, isopropyl acetate to recover the d or l-threo-methylphenidate and the remaining aqueous layer is treated with sulfuric or hydrochloric acid to cause precipitation of L- or D-DPTA, which is recovered by filtration.

In case of recovery of L- or D-DPTA from spent aqueous layers after extraction of d or l-threo-methylphenidate base from basification of the salts, L- or D-DPTA is directly precipitated by treatment with sulfuric or hydrochloric acid and the precipitated L- or D-DPTA is recovered by filtration.

The process of preparation of d-threo-methylphenidate hydrochloride and recovery of D-DPTA salt is shown in Scheme I Scheme I:

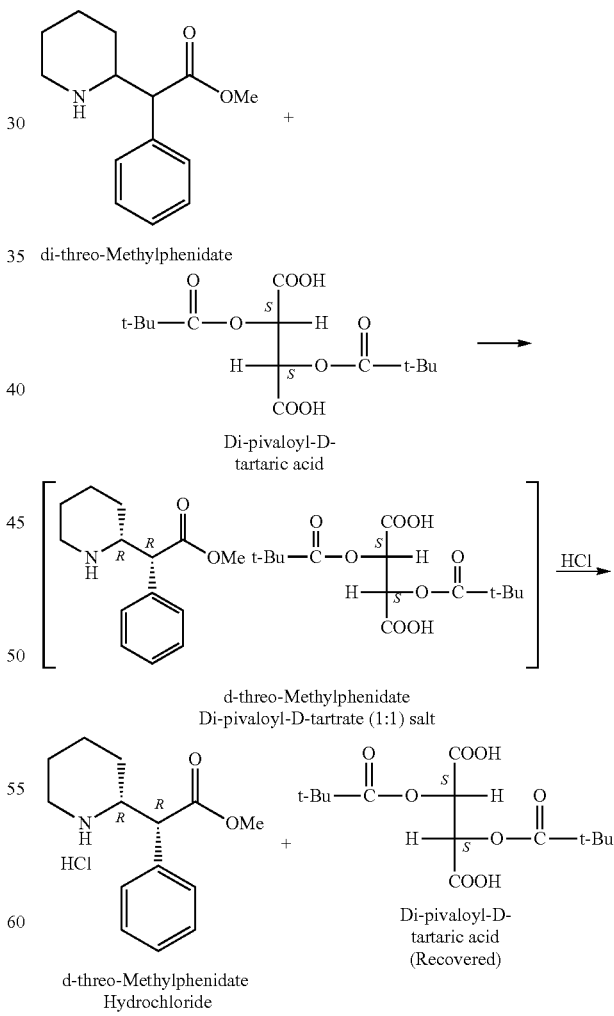

di-threo-Methylphenidate

Di-pivaloyl-D-tartaric acid d-threo-Methylphenidate Di-pivaloyl-D-tartrate (1:1) salt d-threo-Methylphenidate Hydrochloride Di-pivaloyl-D-tartaric acid (Recovered)

In order that this invention to be more fully understood the following preparative and testing examples are set forth.

These examples are for the purpose of illustration only and are not to be construed as limiting the scope of the invention in any way.

Example 1: Preparation of d-Threo-Methylphenidate D-DPTA Salt

Racemic dl-threo-methylphenidate base (100 g) is dissolved in 1.0 L of ethyl acetate. The solution is heated up to 50° C.-55° C. and solution of D-DPTA (150 g) dissolved in 500 ml of ethyl acetate is added to the heated solution. The mixture is stirred at 50° C.-55° C. for 30 min. The obtained mass is cooled to ambient temperature. The mass is further cooled up to 10° C.-15° C. and is stirred for 2 hours at the same temperature. The crystals of d-threo-methylphenidate D-DPTA salt is filtered and washed with 200 ml of chilled ethyl acetate. The crystals are dried at temperature not exceeding 50° C. under vacuum. This results in the yield of 116 g of d-threo-methylphenidate D-DPTA salt, which is equivalent to 98%.

Example 2: Preparation of Dexmethylphenidate Hydrochloride d-threo-methylphenidate D-DPTA salt (100 g) is mixed with 1200 ml of demineralized water. The solution is cooled to a temperature of 10° C.-15° C. and the pH is adjusted to 8-9 by addition of liquor ammonia. The solution is extracted with two parts, each with 400 ml of diisopropyl ether. Wash the diisopropyl ether extract with 200 ml demineralized water and 200 ml of 30% sodium chloride solution. The extract is cooled to 0° C.-5° C. and hydrochloric acid-isopropyl alcohol solution (20% HCl) is added till the pH of the solution is less than 2.0. The solution is continuously stirred at 0° C.-5° C. for 1 hour. The slurry of dexmethylphenidate hydrochloride is formed, which is filtered and the cake is washed with 200 ml of acetone. Finally, the compound is dried at temperature not exceeding 50° C. under vacuum. The yield of dexmethylphenidate hydrochloride is 46 g, which is equivalent to 94.8%.

Example 3: Recovery of D-DPTA from Salt Mother Liquor

The ethyl acetate mother liquor resulted from example 1 is used to recover D-DPTA. The ethyl acetate mother liquor is distilled to obtain pure ethyl acetate. The residue obtained is dissolved in 500 ml of demineralized water and the pH is adjusted to 8-9 by addition of liquor ammonia. The solution is extracted into two parts, each with 400 ml of diisopropyl ether. In another flask, take 500 ml of demineralized water and 55 ml of concentrated hydrochloric acid. Add few crystals of D-DPTA and the mass is chilled up to 10° C.-15° C. Add the ammonical aqueous layer to the acidic water drop wise at 10° C.-15° C. and the solution is stirred for 30 minutes. The precipitate of D-DPTA formed is filtered and washed with 100 ml of demineralized water till neutral pH is achieved. The precipitate is dried at 50° C.-55° C. under vacuum till moisture content is below 0.5%.

Example 4: Recovery of D-DPTA from Spent Aqueous Layer of Dexmethylphenidate Hydrochloride Preparation In addition to the ethyl acetate mother liquor, the D-DPTA is also recovered from the spent aqueous layer of dexmethylphenidate hydrochloride. Take 500 ml of demineralized water in a flask and add 55 ml of concentrated hydrochloric acid. Add few crystals of D-DPTA and chill the mass up to 10° C.-15° C. Add the ammonical aqueous layer drop wise to the acidic water at 10° C.-15° C. and stir the solution for 30 minutes. Filter the precipitate of D-DPTA. The precipitate of D-DPTA formed is filtered and washed with 100 ml of demineralized water till neutral pH is achieved. The precipitate is dried at 50° C.-55° C. under vacuum till moisture content is below 0.5%. The yield of D-DPTA obtained in the example 3 and example 4 is 130 g, which is equivalent to 87%.

What is claimed is:
1. A process for preparation of dexmethylphenidate hydrochloride from racemic methylphenidate, the process comprises the steps of:
   a. treating racemic mixture of dl-threo-methylphenidate base in the presence of a resolving agent in a solvent to isolate corresponding dipivaloyl tartrate salt of d-threo-methylphenidate;
   b. treating the dipivaloyl tartrate salt of d-threo-methylphenidate with a base to obtain a d-threo-methylphenidate base;
   c. extracting the d-threo-methylphenidate base using a solvent;
   d. treating the extracted d-threo-methylphenidate base with hydrochloric acid-isopropyl alcohol solution to obtain d-threo-methylphenidate hydrochloride in the form of slurry;
   e. filtering dexmethylphenidate hydrochloride slurry and washing with acetone; and
   f. recovering the resolving agent from the salt mother liquor and from the spent aqueous layer of dexmethylphenidate hydrochloride.

2. The process as claimed in claim 1, wherein the resolving agent used is a di-pivaloyl-D-tartaric acid (D-DPTA).

3. The process as claimed in claim 1, wherein the solvent used to dissolve racemic mixture of dl-threo-methylphenidate base is selected from a group consisting of acetonitrile, ethyl acetate, isopropyl acetate, acetone, methyl ethyl ketone, isobutyl methyl ketone, methylene chloride, ethylene dichloride, C1-C4 lower aliphatic alcohol and water.

4. The process as claimed in claim 1, wherein the base used to treat the d-threo-methylphenidate salt is selected from a group consisting of sodium hydroxide, potassium hydroxide, sodium bi-carbonate, sodium carbonate, potassium carbonate, ammonium hydroxide and triethylamine.

5. The process as claimed in claim 1, wherein the solvent used for extraction of methylphenidate base is selected from a group consisting of diethyl ether, diisopropyl ether, chloroform, methylene chloride, hexane, ethylene dichloride, toluene, benzene, xylene, ethyl acetate and isopropyl acetate.

6. The process as claimed in claim 1, wherein the process is carried at the temperature in the range between 30° C. and the boiling point of the solvent used.

7. The process as claimed in claim 1, wherein the molar ratio of di-pivaloyl-D-tartaric acid and the racemic mixture of dl-threo-methylphenidate base used are in the range of 0.25:1 and 2:1.

8. The process as claimed in claim 1, wherein the process for recovering the resolving agent from the salt mother liquor comprises the steps of:
   a. distilling the solvent mother liquor to obtain a pure residue of the solvent used;
   b. dissolving the solvent residue in demineralised water and adjusting the pH to 8-9 using a liquid ammonia;

c. extracting the solution with two equal parts of diisopropyl ether;
d. adding crystals of di-pivaloyl-D-tartaric acid into a solution of 500 ml of demineralized water and 55 ml of concentrated hydrochloric acid and chilling the solution to 10° C.-15° C. with continuous stirring;
e. adding ammonical aqueous layer to the acidic water drop wise at 10° C.-15° C. and stirring the solution is for 30 minutes to form the precipitate of D-DPTA;
f. filtering the D-DPTA precipitate and washing with demineralized water; and
g. drying the precipitate at 50° C.-55° C. under vacuum till moisture content is below 0.5%.

9. The process as claimed in claim 1, wherein the process for recovering the resolving agent from the spent aqueous layer of dexmethylphenidate hydrochloride comprises the steps of:
a. adding crystals of di-pivaloyl-D-tartaric acid into a solution of 500 ml of demineralized water and 55 ml of concentrated hydrochloric acid and chilling the solution to 10° C.-15° C. with continuous stirring;
b. adding ammonical aqueous layer to the acidic water drop wise at 10° C.-15° C. and stirring the solution is for 30 minutes to form the precipitate of D-DPTA;
c. filtering the D-DPTA precipitate and washing with demineralized water; and
d. drying the precipitate at 50° C.-55° C. under vacuum till moisture content is below 0.5%.

10. The process as claimed in claim 8, wherein the yield of the D-DPTA recovered is 87%.

* * * * *